United States Patent [19]

Fukumura et al.

[11] 3,998,817
[45] Dec. 21, 1976

[54] PROCESS FOR PRODUCING CEPHALOSPORANIC ACID DERIVATIVES

[75] Inventors: Masataka Fukumura, Toyonaka; Kaoru Maeshima, Takarazuka; Shigeru Okano, Ibaraki, all of Japan

[73] Assignee: Sumitomo Chemical Company, Limited, Osaka, Japan

[22] Filed: Nov. 14, 1973

[21] Appl. No.: 415,880

[30] Foreign Application Priority Data
Nov. 15, 1972  Japan ............................ 47-115113

[52] U.S. Cl. .................. 260/243 C; 424/246; 260/239.1; 260/306.7 E
[51] Int. Cl.² ...................................... C07D 501/10
[58] Field of Search ........................... 260/243 C

[56] References Cited
UNITED STATES PATENTS

| | | | |
|---|---|---|---|
| 3,275,626 | 9/1966 | Morin et al. | 260/243 C |
| 3,632,850 | 1/1972 | Garbrecht | 260/243 C |
| 3,725,397 | 4/1973 | Graham et al. | 260/243 C |
| 3,725,399 | 4/1973 | Ellerton et al. | 250/243 C |
| 3,852,281 | 12/1974 | Verweij | 260/243 C |
| 3,852,295 | 12/1974 | Graham et al. | 260/243 C |
| 3,862,181 | 1/1975 | Davis et al. | 260/243 C |

*Primary Examiner*—Nicholas S. Rizzo
*Attorney, Agent, or Firm*—Sughrue, Rothwell, Mion, Zinn & Macpeak

[57] ABSTRACT

Novel penicillin derivatives of the formula (I)

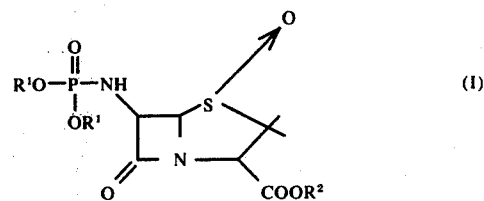

wherein $R^1$ represents a lower alkyl group and $R^2$ represents an ester protective group, as hereinafter defined and 7-amino-3-desacetoxycephalosporanic acid derivatives of the formula (II)

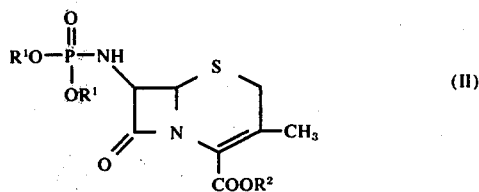

wherein $R^1$ represents a lower alkyl group and $R^2$ represents an ester protective group, which are useful as precursors for the production of cephalosporin derivatives, and an improved process for producing cephalosporin derivatives of the formula (II) above and the formula (III)

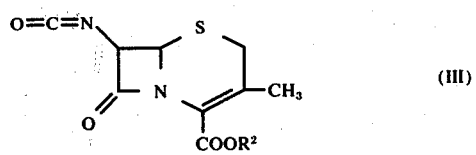

wherein $R^2$ is an ester protective group, are disclosed.

6 Claims, No Drawings

PROCESS FOR PRODUCING CEPHALOSPORANIC ACID DERIVATIVES

BACKGROUND OF THE INVENTION

1. Field of the Invention

This invention relates to a novel process for producing cephalosporin derivatives and novel cephalosporanic acid derivatives. More particularly, this invention relates to an improved process for producing 7-isocyanatocephalosporin derivatives represented by the formula (III) above, which are known to be useful as intermediates for the preparation of cephalosporin derivatives having an excellent antimicrobial activity; to novel 7-amino-3-desacetoxycephalosporanic acid derivatives represented by the formula (II) above, which are useful as intermediates for the preparation of cephalosporin derivatives of the formula (III) above; and to novel penicillin derivatives of the formula (I) above, which can advantageously be used as starting materials for the preparation of the 7-isocyanatocephalosporin derivates represented by the formula (III) above.

2. Description of the Prior Art

It is well known that 7-isocyanatocephalosporin derivatives represented by the formula (III) can be produced from 7-amino-3-desacetoxycephalosporanic acid derivatives as disclosed in Belgian Pat. No. 760,494 and that a wide variety of cephalosporin compounds having a broad spectrum of antimicrobial activity and thus being useful as antibacterial agents can be prepared in the manner described in Belgian Pats. Nos. 760,494 and 775,011, Netherlands Pats. Nos. 7,208,149, 7,205,885, 7,200,486, 7,018,385 and 7,209,964, and German Pat. No. 2,155,081 by taking advantage of the known reactivity of an isocyanate group of the 7-isocyanatocephalosporin derivatives. It is also well known that 6β-acylamidopenicillin sulfoxides can be converted into 7β-acrylamidocephalosporin derivatives by heating the 6β-acylamidopenicillin sulfoxides at a temperature ranging from about 100° C to about 175° C in the presence of an acidic compound as disclosed in U.S. Pat. No. 3,275,626. However, it has not been hitherto known that phosphoric acid amide compounds are generally converted into corresponding isocyanate compounds by treatment with phosgene via dephosphorylation.

However, cephalosporin derivatives having various acyl groups cannot be prepared by converting 6β-acylamidopenicillin sulfoxide derivatives into 7β-acylamidocephalosporin derivatives as disclosed in U.S. Pat. No. 3,275,626. For example, investigations by the present inventors revealed that penicillin sulfoxide derivatives having an ureido group as a side chain can not be used to produce the corresponding cephalosporin derivatives by the procedure taught in U.S. Pat. No. 3,275,626.

An object of the present invention is therfore to provide an improved process for producing the cephalosporin derivatives represented by the formulae (II) and (III).

Another object of this invention is to provide novel 7-amino-3-desacetoxycephalosporanic acid derivatives represented by the formula (II) as hereinbefore defined.

A further object of this invention is to provide novel penicillin derivatives of the formula (I) as hereinbefore defined.

Other objects of the present invention will be apparent from the following description.

SUMMARY OF THE INVENTION

The above objects can be accomplished by the process of the present invention which comprises treating a phosphoric acid amide derivative of penicillin represented by the formula (I)

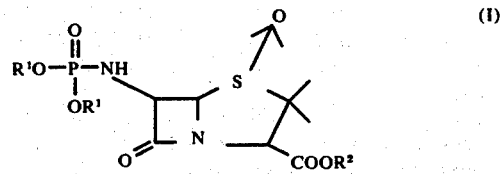

wherein $R^1$ represents a lower alkyl group and $R^2$ represents an ester protective group, with an acidic compound to produce the corresponding 7-amino-3-desacetoxycephalosporanic acid derivative represented by the formula (II)

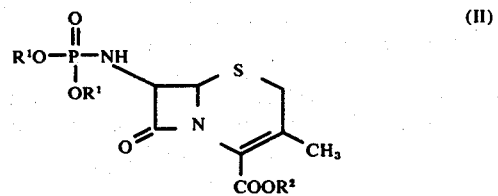

wherein $R^1$ and $R^2$ are as defined above, and reacting the 7-amino-3-desacetoxycephalosporanic acid derivative (II) thus obtained with phosgene in the presence of a tertiary amine base, as an acid acceptor, to produce the corresponding 7-isocyanatocephalosporin derivative represented by the formula (III)

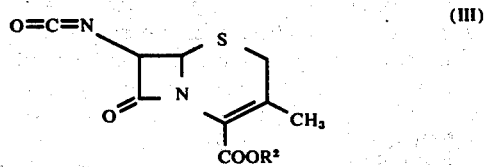

wherein $R^2$ is as defined above.

DETAILED DESCRIPTION OF THE INVENTION

The term "lower alkyl" as used throughout the specification and claims of the present invention in the definition of the substituent $R^1$ means straight or branched alkyl groups having 1 to 4 carbon atoms, such as methyl, ethyl, isopropyl, n-butyl and the like.

The term "ester protective group" used throughout the specification and claims of the present invention means a protective group commonly employed in the synthesis of cephalosporin compounds. Typical examples of such ester protective groups are alkyl groups such as a methyl group, halogenated alkyl groups such as a 2,2,2-trichloroethyl group, aralkyl groups such as a benzyl group, a p-nitrobenzyl group, a p-methoxybenzyl group, a phenacyl group and a benzhydryl group, trialkylsilyl groups such as a trimethylsilyl group, and the like. The ester protective groups and their function are well known in the art and can be freely selected by one skilled in the art so long as the function of protection is achieved.

As a result of extensive studies by the present inventors, it was found that cephalosporanic acid derivatives represented by the formula (II) can easily be produced in high yields directly from the corresponding penicillin phosphoric acid amide derivatives of the formula (I) and that the cephalosporin derivatives represented by the formula (II) can be converted into the corresponding 7-isocyanatocephalosporin derivative represented by the formula (III) by the reaction with phosgene in the presence of a teritary amine base as an acid acceptor.

It is quite unexpected that the conversion of penicillin derivatives into cephalosporin derivatives proceeds even when an amino group at the 6-position of the pencillin derivatives is in the form of a phosporic acid amide shown by the formula (I) and that the phosphoric acid amide compound shown by the formula (II) can be converted into the corresponding isocyanato compounds of the formula (III). The compounds represented by the formulae (II) and (III) of the present invention are novel compounds, not previously described in the literature.

As described above the pencillin sulfoxide derivatives represented by the formula (I) are novel compounds, not previously disclosed in the literature, and can be prepared advantageously and conveniently by any one of the following procedures:

1) 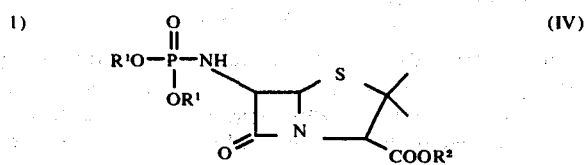 (IV)

Phosphoramidopenicillin derivatives represented by the formula (IV), wherein $R^1$ and $R^2$ are as defined above, can be oxidized with a peroxide in an inert solvent. A suitable peroxide which can be employed in the reaction is, for example, peracetic acid, monopermaleic acid, m-chloroperbenzoic acid, ozone and the like. The reaction is preferably carried out at relatively low temperature at which decomposition of the β-lactam ring and the peroxide does not occur, but a temperature between about -20° C and room temperature (about 20° to 30° C) is practically convenient. Phosphoramidopenicillin derivatives represented by the formula (IV) are novel compounds and can be prepared by the reaction of 6-aminopenicillanic acid or its derivative with a dialkylhalophosphate.

2) 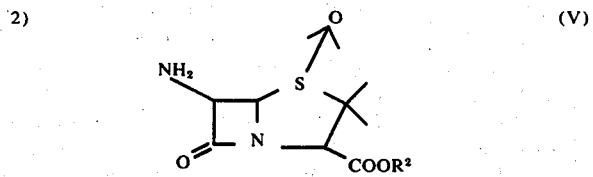 (V)

6-Aminopenicillanic acid (hereinafter referred to as 6-APA) sulfoxide derivatives represented by the formula (V), wherein $R^2$ is as defined above, are allowed to react with a dialkylhalophosphate represented by the formula (VI)

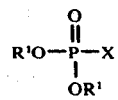 (VI)

wherein $R^1$ is as defined above, and X represents a halogen atom, in an inert solvent at a temperature at which decomposition of the β-lactam ring does not occur, but a temperature between about -40° C and room temperature is practically convenient. The addition of a base such as, pyridine, quinoline, diethylaniline and the like as an acid acceptor can be favorably employed.

6-APA sulfoxide derivatives represented by the formula (V) are the novel compounds and can be prepared as follows. Penicillin-G (or - V) sulfoxide derivatives of the formula (VII)

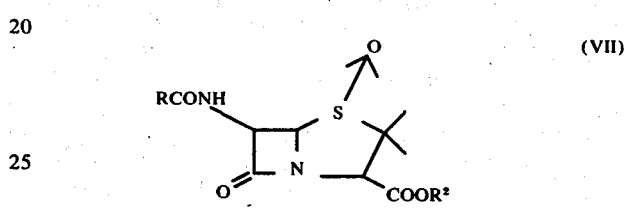 (VII)

wherein R is a $C_6H_5CH_2$ group or a $C_6H_5OCH_2$ group, and $R^2$ is an ester protective group, is treated with phosphorus pentachloride in an inert solvent in the presence of a base to give the corresponding iminochloride, which is then treated with a lower alcohol to give the corresponding iminoether. The iminoether thus obtained is hydrolyzed by contacting with water to give 6-APA sulfoxide derivatives of the formula (V). Suitable examples of inert solvents are chloroform, dichloromethane, toluene and the like. Phosphorus pentachloride is generally used in an excess amount, preferably in an amount of more than 2 molar excess per mole of the penicillin derivatives. The preferable reaction temperature range is from about -40° C to 0° C. Suitable examples of the base as an acid acceptor are tertiary amines, for example, pyridine, quinoline, diethylaniline, etc. The iminochloride thus obtained may be isolated, however generally the reaction mixture is treated with an excess amount of alcohol to produce the iminoether. The examples of a lower alcohol are methanol, ethanol, iso-propanol, n-butanol and the like. The reaction proceeds smoothly at the same temperature as the iminochloridation described above. The hydrolysis is preferably carried out at relatively low temperatures at which decomposition of the β-lactam ring does not occur, and temperatures between about -10° and 10° C are practically convenient.

3. Penicillin-G (or - V) sulfoxide derivatives are allowed to react with a phosphorus pentahalide, followed by an alcohol to produce the corresponding iminoether which is treated with an alkali. The reaction of penicillin-G (or - V) sulfoxide derivatives with the phosphorus pentahalide is conducted in an inert anhydrous solvent in the presence of a tertiary amine base as an acid acceptor. Suitably examples of these solvents are chloroform, dichloromethane, toluene and the like. Phosphorus pentachloride is generally used in an excess amount, preferably in an amount of more than 2 molar excess per mole of the penicillin derivatives. The preferable reaction temperature ranges from about -40° C to 0° C. Suitable examples of bases which can be used as an acid acceptor are tertiary amines, for example, pyridine, quinoline, diethylaniline, etc. The iminochloride thus obtained may be isolated, however, generally the reaction mixture is treated with an excess amount of alcohol to produce the iminoether. The examples of a lower alcohol are methanol, ethanol, iso-propanol, n-butanol and the like. The reaction proceeds smoothly at the same temperature as the iminochloridation described above. The iminoether thus obtained, without isolation, is treated with an excess amount of a base of yield the phosphoramide represented by the formula (I). The examples of a base are a tertiary amine, such as, pyridine, quinoline, diethylaniline and the like, or an inorganic base such as sodium bicarbonate, sodium carbonate and the like.

The conversion of the pencillin sulfoxide derivative of the formula (I) into the 7-amino-3-desacetoxycephalosporanic acid derivative of the formula (II) can be carried out in an inert solvent, preferably a solvent which can form an azeotropic mixture with water. Suitable examples of water azeotroping solvents which can be used in the conversion of (I) into (II) are aromatic hydrocarbon solvents such as benzene and toluene, aliphatic halogenated hydrocarbon solvents such as dichloroethane, cyclic ethers such as dioxane, nitrile solvents such as acetonitrile, ketones such as methylisobutylketone, and the like. In this conversion, better results can sometimes be obtained by using a tertiary amide as a solvent in place of a portion of or all of the above inert solvent. Typical examples of the teritary amides are dimethylformamide, dimethylacetamide, etc. Dioxane and a mixture of dichloroethane and dimethylformamide are preferred. A broad range of concentrations can be used and the concentration range employed is not limited. The preferable concentration of the compound (I) is 1 to 20% by weight. Although the conversion can be carried out over a wide range of reaction temperatures higher than room temperature (e.g., about 20° to 30° C), it is generally preferred to carry out the conversion at the reflux temperature of the solvent used while azeotropically removing the water formed during the conversion reaction from the reaction system. A particularly preferred temperature range is from about 80° to about 170° C.

The water formed during the reaction can also be removed from the reaction system by treatment with a dehydrating agent such as those generally used in organic syntheses, for example, calcium chloride, magnesium sulfate, calcium oxide, molecular sieves, etc. In this instance, it is advantageous that the reaction solvent distilled off as an azeotropic mixture be dehydrated with the above dehydrating agent and then the dehydrated solvent be returned to the reaction system. For this purpose, an apparatus such as Soxhlet, a Dean-Stark trap, etc. can advantageously be used with good results.

The conversion reaction is conducted in the presence of a catalytic amount of an acidic compound. Suitably examples of acidic compounds which can be used in the conversion reaction are organic acids, for example, sulfonic acids such as methanesulfonic acid, para-toluenesulfonic acid, naphthalenesulfonic acid and the like, organic phosphonic acids such as methanephosphonic acid, dichloromethanephosphonic acid and phosphonic acid monoester such as the monomethyl or monophenyl ester, carboxylic acids having 2 to 5 carbon atoms or the anhydrides thereof, such as acetic acid, propionic acid and the like and the anhydrides of these acids, and mineral acids such as phosphoric acid, sulfuric acid and the like. In some cases, the carboxylic acid anhydrides such as acetic anhydride can be used as the solvent and serves a dual function as the solvent and the acid compound. In addition, the acidic compound employed can be a salt of a strong acid and a weak base, e.g., having a pKb more than 4, for example, pyridine phosphate, pyridine mono-O-substituted orthophosphate, quinoline hydrochloride and the like. A molar ratio of the acidic compound of 0.001 to 0.5, preferably 0.01 to 0.2, to the amount of compound (I) is generally suitable.

The formation of an isocyanato compound from the cephalosporin derivatives represented by the formula (II) is preferably carried out in an inert organic solvent in the presence of an acid acceptor. The reaction should preferably be accomplished in an anhydrous inert solvent. Halogenated hydrocarbon solvents such as methylene chloride or chloroform are particularly suitable for this purpose. Generally, since phosgene is easily handled as a solution in inert solvents such as an aromatic or aliphatic hydrocarbon, e.g., toluene, the isocyanato formation reaction is advantageously conducted in a solvent mixture comprising methylene chloride or chloroform and toluene. Use of phosgene in such a solvent is not essential, however. However, the reaction was found to proceed slowly in a solvent consisting of an aromatic hydrocarbon alone such as toluene. A broad range of concentrations can be used and the concentration range employed is not limited. The preferable concentration of the compound (II) is 1 to 20% by weight.

Suitable examples of the base used as an acid acceptor are tertiary amines such as triethylamine, diethylaniline, pyridine, etc., basic ion-exchange resins, and heterocyclic amines such as pyridine, picoline and quinoline and the like are particularly preferred. An about equivalent amount of acid acceptor to about a 10:1 or 20:1 molar excess to the amount of compound (II) is generally suitable.

The reaction is preferably carried out at relatively low temperatures at which decomposition of the β-lactam ring does not occur, but temperatures between ice-cooling (e.g., 0° to 5° C) temperatures and room temperatures (e.g., 20° to 30° C) are practically convenient. Phosgene is generally used in an excess amount with respect to the cephalosporin derivative (II), preferably in molar excess of 3 to 10 moles per 1 mole of the cephalosporin derivative.

The present invention is further illustrated in greater detail by the following Examples, but they are not to be construed as limiting the scope of this invention. Unless otherwise indicated, all parts and percents are by weight.

EXAMPLE 1

To 90 ml of anhydrous dioxane was added 3.0 g of 2,2,2-trichloroethyl 6β-dimethylphosphoramidopenicillanate 1-oxide and 0.3 g of dichloromethanephosphoric acid pyridinium salt, and the resulting mixture was refluxed for 5.5 hrs. while recycling the condensed distillate into the reaction flask through a column packed with a Linde 3A molecular sieve (produced by Showa Union). After the reaction was completed, the reaction mixture was concentrated under reduced pressure using an aspirator and the residue was dissolved in chloroform and washed with water. The chloroform layer was dried over anhydrous magnesium sulfate and concentrated under reduced pressure using an aspirator. The resulting residue was chromatographed over a Florisil (Magnesium silicate) column which was eluted with chloroform to give 2.4 g of 2,2,2-trichloroethyl 3-methyl-7β-dimethylphosphoramido-ceph3-em-4-carboxylate as an amorphous solid after removal of the solvent from the eluates.

| | |
|---|---|
| $(\alpha)_D^{20} = +73.2$ (C=1, CHCl$_3$) | |
| IR: $\nu$max (Nujol) | : $\nu_{C=O}$ 1790 and 1760 cm$^{-1}$ |
| NMR (CDCl$_3$) | : Δ2.22 ppm (3-CH$_3$) |

EXAMPLE 2

In a mixture of 100 ml of dichloroethane and 50 ml of dimethylformamide was dissolved 5.0 g of 2,2,2-trichloroethyl 6β-dimethylphosphoramidopenicillanate 1-oxide and 0.2 g of methanesulfonic acid, and the mixture was refluxed for 15 hours. During the reaction the condensed distillate was recycled in the same manner as described in Example 1. After completion of the reaction, the reaction mixture was evaporated to dryness under reduced pressure using an aspirator, and the residue chromatographed over a Florisil column which was eluted with chloroform. Removal of the solvent from the eluates gave 3.7 g of 2,2,2-trichloroethyl 3-methyl-7β-dimethylphosphoramido-ceph-3-em-4-carboxylate as an amorphous solid.

The IR and NMR spectra of the product were indentical with those of the product obtained in Example 1.

EXAMPLE 3

To 20 ml of anhydrous dioxane was added 1.0 g of methyl 6β-dimethylphosphoramidopenicillanate 1-oxide and 0.1 g of dichloromethanephosphoric acid pyridinium salt, and the resulting mixture was refluxed for 8 hours and worked up in the same manner as described in Example 1 to give 0.55 g of methyl 3-methyl-7β-dimethylphosphoramido-ceph-3-em-4-carboxylate as an oil.

| | |
|---|---|
| IR : $\nu$max (CHCl$_3$) | : $\nu_{C=O}$ 1780 and 1725 cm$^{-1}$ |
| NMR(CDCl$_3$) | : Δ2.15 ppm (3-CH$_3$) |

EXAMPLE 4

To 50 ml of anhydrous dioxane was added 3.0 g of 2,2,-trichloroethyl 6β-diethylphosphoramidopenicillanate 1-oxide and 0.2 g of dichloromethanephosphoric acid pyridinium salt, and the resulting mixture refluxed for 8 hours and worked up in the same manner as described in Example 1 to give 1.8 g of 2,2,2-trichloroethyl 3-methyl-7β-diethylphosphoramido-ceph-3-em-4-carboxylate as an amorphous solid.

| | |
|---|---|
| IR : $\nu$max (CHCl$_3$) | : $\nu_{C=O}$ 1780 and 1760 cm$^{-1}$ |
| NMR (CDCl$_3$) | : Δ2.20 ppm (3-CH$_3$) |

EXAMPLE 5

By the same procedure as described in Example 1 using 2.0g of 2,2,2-trichloroethyl 6β-di(n-butyl)phosphoramidopenicillanate 1-oxide, 1.3 g of 2,2,2-trichloroethyl-3-methyl-7β-di(n-butyl)-phosphoramido-ceph-3-em-4-carboxylate was obtained as an oil.

| | |
|---|---|
| IR : $\nu$max (CHCl$_3$) | : $\nu_{C=O}$ 1785 and 1760 cm$^{-1}$ |
| NMR (CDCl$_3$) | : Δ2.20 ppm (3-CH$_3$) |

Example 6

A suspension of 6.9 g of phosphorus pentachloride in 60 ml of dichloromethane was added dropwise to a cooled solution of 8.0 of 2,2,2-trichloroethyl 6β-phenylacetamidopenicillanate 1-oxide and 7.5 g of diethylaniline dissolved in 200 ml of dichloromethane with the temperature being kept at -20° C. The mixture was stirred for 2 hours at the same temperature. 80 ml of methanol was added dropwise thereto over a 15 minute period at a temperature between −15° C and −20° C and stirring was continued for an additional 3 hours at this temperature. To the mixture was added 42 g of sodium bicarbonate and the mixture stirred at 0° to 5° C for 14 hours, and filtered. The filtrate was washed successively with 1N hydrochloric acid and an aqueous sodium bicarbonate solution. The dichloromethane later was concentrated under reduced pressure to give 12.1 g of the residue, which was triturated with petroleum ether and diethyl ether to give 6.8 g of 2,2,2-trichloroethyl 6β-dimethylphosphoramidopenicillanate 1-oxide having a melting point of 129.5° to 131° C.

IR : $\nu_{max}$ (Nujol) : $\nu_{C=O}$ 1800 and 1765 cm$^{-1}$

To 30 ml of anhydrous dioxane was added 6.0 g of the product thus obtained and 0.12 g of dichloromethanephosphoric acid pyridinium salt, and the mixture was refluxed for 6 hours during which time the water produced in the reaction was removed azeotropically as described in Example 1. The mixture was concentrated under reduced pressure, the residue dissolved in benzene, washed successively with 1N hydrochloric acid and an aqueous sodium bicarbonate solution, dried over anhydrous magnesium sulfate and concentrated under reduced pressure. The crude product thus obtained was triturated with diethyl ether to give 4.7 g of 2,2,2-trichloroethyl 3-methyl-7β-dimethylphosphoramido-ceph-3-em-4-carboxylate as a pale yellow amorphous solid.

The IR and NMR spectra of the product were identical with those of the product obtained in Example 1.

EXAMPLE 7

A suspension of 12.9 g of phosphorus pentachloride in 130 ml of dichloromethane was added dropwise to a cooled solution of 10.0 g of p-nitrobenzyl 6β-phenylacetamidopenicillanate 1-oxide and 8.0 g of diethylaniline in 100 ml of dichloromethane while keeping the temperature at −20° C. The mixture was stirred for 2 hours at the same temperature, and 60 ml of methanol was added dropwise thereto over a 20 minute period at a temperature between −15° C and −20° C. The mixture was stirred for an additional 1 hour at this temperature, mixed with 91 g of diethylaniline, and stirred for 16 hours at 0° to 5° C.

The reaction mixture was washed with 1N hydrochloric acid, then with aqueous sodium bicarbonate solution, dried over anhydrous magnesium sulfate, and concentrated under reduced pressure. The residue was triturated with petroleum ether and diethyl ether to give 7.0 g of p-nitrobenzyl 6β-dimethylphosphoramidopenicillanate 1-oxide as an amorphous solid. To 50 ml of anhydrous dioxane was added 4.8 g of the product thus obtained and 0.07 g of methanesulfonic acid pyridinium salt. The mixture was refluxed for 6 hours and worked up in the same manner as described in Example 6 to give 2.6 g of p-nitrobenzyl 3-methyl-7β-dimethyl-phosphoramido-ceph-3-em-4-carboxylate as an amorphous solid.

| IR : νmax(CHCl₃) | : νc=o 1780 and 1760 cm⁻¹ |
|---|---|
| NMR (CDCl₃) | : Δ2.15 ppm (3-CH₃) |

EXAMPLE 8

In 50 ml of dichloromethane was dissolved 4.6 g of 2,2,2-trichloroethyl 6β-dimethylphosphoramidopenicillanate at −10° C, and a solution of 2.2 g of m-chloroperbenzoic acid and 20 ml of dichloromethane was added dropwise thereto over a 10 minute period at the same temperature under stirring. The mixture was stirred for 1 hour at this temperature, washed with aqueous sodium bicarbonate solution, dried over anhydrous magnesium sulfate, and concentrated under reduced pressure to give 4.7 of 2,2,2-trichloroethyl 6β-dimethylphosphoramidopenicillanate 1-oxide as an amorphous solid. The product thus obtained was dissolved in 150 ml of acetic anhydride and refluxed for 40 minutes. After the completion of the reaction, the reaction mixture was concentrated under reduced pressure. The residue was dissolved in ethyl acetate, washed with aqueous sodium bicarbonate solution, dried over anhydrous magnesium sulfate, and concentrated under reduced pressure. The residue was worked up in the same manner as described in Example 1 to give 2.2 g of 2,2,2-trichloroethyl 3-methyl-7β-dimethylphosphoramido-ceph-3-em-4-carboxylate as an amorphous solid.

The IR and NMR spectra of the product were identical with those of the product obtained in Example 1.

EXAMPLE 9

To a mixture of 50 ml of dichloromethane, 3.7 g of p-nitrobenzyl 6-aminopenicillanate 1-oxide and 1.6 g of diethylaniline was added 1.5 g of dimethyl chlorophosphate at 0° to 5° C over a 5 minute period with stirring. The mixture was stirred at the same temperature for 2 hours, washed with 1N hydrochloric acid and an aqueous sodium bicarbonate solution, dried over anhydrous magnesium sulfate, and concentrated under reduced pressure to give 4.4 g of p-nitrobenzyl 6β-dimethyl-phosphoramidopenicillanate 1-oxide as an amorphous solid. To 50 ml of anhydrous dioxane was added 4.4 g of the product thus obtained and 0.09 g of dichloromethanephophoric acid pyridinium salt. The mixture was refluxed for 6 hours and worked up in the same manner as described in Example 6 to give 4.1 g of p-nitrobenzyl 3-methyl-7β-dimethylphosphoramido-ceph-3-em-4-carboxylate as an amorphous solid.

The IR and NMR spectra of the product were identical with those of the product obtained in Example 7.

EXAMPLE 10

In 30 ml of anhydrous, methanol-free dichloromethane was dissolved 3.0 g of 2,2,2-trichloroethyl 3-methyl-7β-dimethylphosphoramido-ceph-3-em-4-carboxylate and 3.1 g of pyridine at 0° to 5° C, and 18 ml of a 30.5% phosgene-toluene solution was added dropwise thereto. The reaction mixture was stirred at 20° to 25° C under a nitrogen stream for 4 hours and then diluted with anhydrous benzene. The precipitated pyridine hydrochloride was removed by filtration in a nitrogen atmosphere, and the filtrate concentrated under reduced pressure to give 2.3 g of 2,2,2-trichloroethyl 3-methyl-7β-isocyanato-ceph-3-em-4-carboxylate as an oil.

| IR : νmax (CHCl₃) | : νNco 2280 cm⁻¹ |
|---|---|
| | νc=o 1790 and 1740 cm⁻¹ |
| Mol. Wt. (Mass Spectrometry) : 370 (theoretical value : 370) | |

EXAMPLE 11

In 40 ml of anhydrous, methanol-free dichloromethane was dissolved 4.2 g of 2,2,2-trichloroethyl 3-methyl-7β-dimethylphosphoramido-ceph-3-em-4-carboxylate and 4.4 g of pyridine, and 25 ml of a 30.5% phosgene-toluene solution was added dropwise to the mixture at 0° to 5° C. The mixture was stirred at this temperature for 5 hours under a nitrogen stream, treated with formic acid to decompose the unreacted phosgene, washed rapidly with cold 1N hydrochloric acid and then with a cold aqueous sodium bicarbonate solution, dried over anhydrous magnesium sulfate, and concentrated under reduced pressure to give 2.8 g of 2,2,2-trichloroethyl 3-methyl-7β-isocyanato-ceph-3-em-4-carboxylate as an oil.

The IR and NMR spectra of the product were identical with those of the product obtained in Example 10.

EXAMPLE 12

In 25 ml of anhydrous, methanol-free dichloromethane was dissolved 2.5 g of p-nitrobenzyl 3-methyl-7β-dimethyl-phosphoramido-ceph-3-em-4-carboxylate and 2.6 g of pyridine, and 15 ml of a 30.5% phosgene-toluene solution was added dropwise to the mixture at 0° to 5° C. The mixture was stirred at this temperature for 5 hours under a nitrogen stream. The reaction mixture was worked up in the same manner as described in Example 10 to give 1.8 g of p-nitrobenzyl 3-methyl-7β-isocyanato-ceph-3-em-4-carboxylate as an oil.

| IR: νmax (CHCl₃) | : νNco 2280 cm⁻¹ |
|---|---|
| | νc=o 1780 and 1730 cm⁻¹ |

While the invention has been described in detail and with reference to specific examples thereof, it will be apparent to one skilled in the art that various changes and modifications can be made therein without departing from the spirit and scope thereof.

What is claimed is:

1. A process for producing a compound of formula (II)

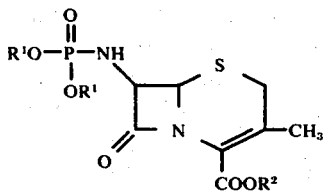

wherein $R^1$ is a $C_1 - C_4$ alkyl group and $R^2$ is an ester protective group selected from the group consisting of methyl, 2,2,2-trichloroethyl, benzyl, p-nitrobenzyl, p-methoxybenzyl, penacyl, benzhydryl and trimethylsilyl, which comprises the step of treating a compound of formula (I)

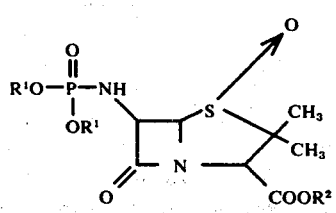

wherein $R^1$ and $R^2$ are as defined above, with an acidic compound selected from the group consisting of meth- anesulfonic acid, p-toluenesulfonic acid, naphthalenesulfonic acid, methanephosphonic acid, dichloromethanephosphonic acid, monomethylphosphonate, monophenylphosphonate, acetic acid, propionic acid, acetic anhydride, propionic anhydride, phosphoric acid, sulfuric acid, phyridine phophate, pyridine mono-o-substitued orthophosphate and quinoline hydrochloride, the amount of said acidic compound being from 0.01 to 0.2 mole per one mole of said compound (I), in at least one inert solvent selected from the group consisting of benzene, toluene, dichloroethane, dioxane, acetonitrile, methyl isobutyl ketone, dimethylformamide and dimethylacetamide at a temperature ranging from about 80° to about 170° C 2. The process according to claim 1, wherein said inert solvent is dioxane or a mixture or dichlorethane and dimethylformamide.

3. The process according to claim 1, wherein said treating with said acidic compound is using a dehydrating agent.

4. The process according to claim 1, wherein the concentration of said compound (I) is 1 to 20% by weight.

5. The process according to claim 1, wherein said $R^1$ is a methyl group.

6. The process according to claim 1, wherein said $R^2$ is a 2,2,2-trichloroethyl group or a -nitrobenzyl group.

* * * * *